United States Patent
Grichnik et al.

(10) Patent No.: US 7,487,134 B2
(45) Date of Patent: Feb. 3, 2009

(54) MEDICAL RISK STRATIFYING METHOD AND SYSTEM

(75) Inventors: Anthony J. Grichnik, Peoria, IL (US); Michael Seskin, Cardiff, CA (US)

(73) Assignee: Caterpillar Inc., Peoria, IL (US)

( * ) Notice: Subject to any disclaimer, the term of this patent is extended or adjusted under 35 U.S.C. 154(b) by 276 days.

(21) Appl. No.: 11/257,341

(22) Filed: Oct. 25, 2005

(65) Prior Publication Data
US 2007/0179769 A1 Aug. 2, 2007

(51) Int. Cl.
*G06F 17/00* (2006.01)
*G06F 7/60* (2006.01)
*G06N 5/02* (2006.01)

(52) U.S. Cl. .................... 706/60; 706/46; 703/2
(58) Field of Classification Search ............ 706/60
See application file for complete search history.

(56) References Cited

U.S. PATENT DOCUMENTS

| | | | |
|---|---|---|---|
| 3,316,395 A | 4/1967 | Lavin | |
| 4,136,329 A | 1/1979 | Trobert | |
| 4,533,900 A | 8/1985 | Muhlberger et al. | |
| 5,014,220 A | 5/1991 | McMann et al. | |
| 5,163,412 A | 11/1992 | Neu et al. | |
| 5,262,941 A | 11/1993 | Saladin et al. | |
| 5,341,315 A | 8/1994 | Niwa et al. | |
| 5,386,373 A | 1/1995 | Keeler et al. | |
| 5,434,796 A | 7/1995 | Weininger | |
| 5,539,638 A | 7/1996 | Keeler et al. | |
| 5,548,528 A | 8/1996 | Keeler et al. | |
| 5,561,610 A | 10/1996 | Schricker et al. | |
| 5,566,091 A | 10/1996 | Schricker et al. | |
| 5,585,553 A | 12/1996 | Schricker | |
| 5,594,637 A * | 1/1997 | Eisenberg et al. | 705/2 |
| 5,598,076 A | 1/1997 | Neubauer et al. | |
| 5,604,306 A | 2/1997 | Schricker | |
| 5,604,895 A | 2/1997 | Raimi | |

(Continued)

FOREIGN PATENT DOCUMENTS

EP 1103926 5/2001

(Continued)

OTHER PUBLICATIONS

Genichi Taguchi, Rajesh Jugulum, The Mahalanobis Taguchi Strategy, A Pattern Technology System, John Wiley & Sons, Inc., 2002.

(Continued)

*Primary Examiner*—David R Vincent
*Assistant Examiner*—Melissa J Berman
(74) *Attorney, Agent, or Firm*—Finnegan, Henderson, Farabow, Garrett & Dunner

(57) ABSTRACT

A method is provided for a medical risk stratification system. The method may include establishing a medical risk process model indicative of interrelationships between a plurality of medical risks and a plurality of health parameters and obtaining a set of values corresponding to the plurality of health parameters. The method may also include calculating the values of the plurality of medical risks simultaneously based upon the set of values corresponding to the plurality of health parameters and the medical risk process model and presenting the values of the plurality of medical risks.

21 Claims, 7 Drawing Sheets

U.S. PATENT DOCUMENTS

| | | | |
|---|---|---|---|
| 5,608,865 A | 3/1997 | Midgely et al. |
| 5,666,297 A | 9/1997 | Britt et al. |
| 5,682,317 A | 10/1997 | Keeler et al. |
| 5,698,780 A | 12/1997 | Mizutani et al. |
| 5,727,128 A | 3/1998 | Morrison |
| 5,750,887 A | 5/1998 | Schricker |
| 5,752,007 A | 5/1998 | Morrison |
| 5,835,902 A | 11/1998 | Jannarone |
| 5,842,202 A | 11/1998 | Kon |
| 5,914,890 A | 6/1999 | Sarangapani et al. |
| 5,925,089 A | 7/1999 | Fujime |
| 5,950,147 A | 9/1999 | Sarangapani et al. |
| 5,966,312 A | 10/1999 | Chen |
| 5,987,976 A | 11/1999 | Sarangapani |
| 6,086,617 A | 7/2000 | Waldon et al. |
| 6,092,016 A | 7/2000 | Sarangapani et al. |
| 6,119,074 A | 9/2000 | Sarangapani |
| 6,145,066 A | 11/2000 | Atkin |
| 6,195,648 B1 | 2/2001 | Simon et al. |
| 6,199,007 B1 | 3/2001 | Zavarehi et al. |
| 6,208,982 B1 | 3/2001 | Allen, Jr. et al. |
| 6,223,133 B1 | 4/2001 | Brown |
| 6,236,908 B1 | 5/2001 | Cheng et al. |
| 6,240,343 B1 | 5/2001 | Sarangapani et al. |
| 6,269,351 B1 | 7/2001 | Black |
| 6,298,718 B1 | 10/2001 | Wang |
| 6,370,544 B1 | 4/2002 | Krebs et al. |
| 6,405,122 B1 | 6/2002 | Yamaguchi |
| 6,438,430 B1 | 8/2002 | Martin et al. |
| 6,442,511 B1 | 8/2002 | Sarangapani et al. |
| 6,477,660 B1 | 11/2002 | Sohner |
| 6,513,018 B1 | 1/2003 | Culhane |
| 6,546,379 B1 | 4/2003 | Hong et al. |
| 6,584,768 B1 | 7/2003 | Hecker et al. |
| 6,594,989 B1 | 7/2003 | Hepburn et al. |
| 6,698,203 B2 | 3/2004 | Wang |
| 6,711,676 B1 | 3/2004 | Zomaya et al. |
| 6,721,606 B1 | 4/2004 | Kaji et al. |
| 6,725,208 B1 | 4/2004 | Hartman et al. |
| 6,763,708 B2 | 7/2004 | Ting et al. |
| 6,775,647 B1 | 8/2004 | Evans et al. |
| 6,785,604 B2 | 8/2004 | Jacobson |
| 6,810,442 B1 | 10/2004 | Lin et al. |
| 6,823,675 B2 | 11/2004 | Brunell et al. |
| 6,859,770 B2 | 2/2005 | Ramsey |
| 6,859,785 B2 | 2/2005 | Case |
| 6,865,883 B2 | 3/2005 | Gomulka |
| 6,882,929 B2 | 4/2005 | Liang et al. |
| 6,895,286 B2 | 5/2005 | Kaji et al. |
| 6,935,313 B2 | 8/2005 | Jacobson |
| 6,941,287 B1 | 9/2005 | Vaidyanathan et al. |
| 6,952,662 B2 | 10/2005 | Wegerich et al. |
| 6,976,062 B1 | 12/2005 | Denby et al. |
| 7,000,229 B2 | 2/2006 | Gere |
| 7,024,343 B2 | 4/2006 | El-Ratal |
| 7,027,953 B2 | 4/2006 | Klein |
| 7,035,834 B2 | 4/2006 | Jacobson |
| 7,117,079 B2 | 10/2006 | Streichsbier et al. |
| 7,124,047 B2 | 10/2006 | Zhang et al. |
| 7,127,892 B2 | 10/2006 | Akins et al. |
| 7,174,284 B2 | 2/2007 | Dolansky et al. |
| 7,178,328 B2 | 2/2007 | Solbrig |
| 7,191,161 B1 | 3/2007 | Rai et al. |
| 7,194,392 B2 | 3/2007 | Tuken et al. |
| 7,213,007 B2 | 5/2007 | Grichnik |
| 7,356,393 B1 | 4/2008 | Schlatre et al. |
| 7,369,925 B2 | 5/2008 | Morioka et al. |
| 2002/0014294 A1 | 2/2002 | Okano et al. |
| 2002/0016701 A1 | 2/2002 | Duret et al. |
| 2002/0042784 A1 | 4/2002 | Kerven et al. |
| 2002/0049704 A1* | 4/2002 | Vanderveldt et al. ........... 707/1 |
| 2002/0103996 A1 | 8/2002 | LeVasseur et al. |
| 2002/0198821 A1 | 12/2002 | Munoz |
| 2003/0018503 A1 | 1/2003 | Shulman |
| 2003/0055607 A1 | 3/2003 | Wegerich et al. |
| 2003/0093250 A1 | 5/2003 | Goebel |
| 2003/0126053 A1 | 7/2003 | Boswell et al. |
| 2003/0126103 A1 | 7/2003 | Chen et al. |
| 2003/0130855 A1 | 7/2003 | Babu et al. |
| 2003/0167354 A1 | 9/2003 | Peppers et al. |
| 2003/0187567 A1 | 10/2003 | Sulatisky et al. |
| 2003/0187584 A1* | 10/2003 | Harris ........................ 702/19 |
| 2003/0200296 A1 | 10/2003 | Lindsey |
| 2004/0030420 A1 | 2/2004 | Ulyanov et al. |
| 2004/0034857 A1 | 2/2004 | Mangino et al. |
| 2004/0059518 A1 | 3/2004 | Rothschild |
| 2004/0077966 A1 | 4/2004 | Yamaguchi et al. |
| 2004/0122702 A1* | 6/2004 | Sabol et al. ..................... 705/2 |
| 2004/0122703 A1* | 6/2004 | Walker et al. .................. 705/2 |
| 2004/0128058 A1 | 7/2004 | Andres et al. |
| 2004/0135677 A1 | 7/2004 | Asam |
| 2004/0138995 A1 | 7/2004 | Hershkowitz et al. |
| 2004/0139041 A1 | 7/2004 | Grichnik |
| 2004/0153227 A1 | 8/2004 | Hagiwara et al. |
| 2004/0230404 A1 | 11/2004 | Messmer et al. |
| 2004/0267818 A1 | 12/2004 | Hartenstine |
| 2005/0047661 A1 | 3/2005 | Mauer |
| 2005/0055176 A1 | 3/2005 | Clarke et al. |
| 2005/0091093 A1 | 4/2005 | Bhaskaran et al. |
| 2005/0209943 A1 | 9/2005 | Ballow et al. |
| 2005/0210337 A1 | 9/2005 | Chester et al. |
| 2005/0240539 A1 | 10/2005 | Olavson |
| 2005/0261791 A1 | 11/2005 | Chen et al. |
| 2005/0262031 A1* | 11/2005 | Saidi et al. ..................... 706/21 |
| 2005/0278227 A1 | 12/2005 | Esary et al. |
| 2005/0278432 A1 | 12/2005 | Feinleib et al. |
| 2006/0010057 A1 | 1/2006 | Bradway et al. |
| 2006/0010142 A1 | 1/2006 | Kim et al. |
| 2006/0010157 A1 | 1/2006 | Dumitrascu et al. |
| 2006/0025897 A1 | 2/2006 | Shostak et al. |
| 2006/0026270 A1 | 2/2006 | Sadovsky et al. |
| 2006/0026587 A1 | 2/2006 | Lemarroy et al. |
| 2006/0064474 A1 | 3/2006 | Feinleib et al. |
| 2006/0068973 A1 | 3/2006 | Kappauf et al. |
| 2006/0129289 A1 | 6/2006 | Kumar et al. |
| 2006/0130052 A1 | 6/2006 | Allen et al. |
| 2006/0229753 A1 | 10/2006 | Seskin et al. |
| 2006/0229769 A1 | 10/2006 | Grichnik et al. |
| 2006/0229852 A1 | 10/2006 | Grichnik et al. |
| 2006/0229854 A1 | 10/2006 | Grichnik et al. |
| 2006/0230018 A1 | 10/2006 | Grichnik et al. |
| 2006/0230097 A1 | 10/2006 | Grichnik et al. |
| 2006/0230313 A1 | 10/2006 | Grichnik et al. |
| 2006/0241923 A1 | 10/2006 | Xu et al. |
| 2006/0247798 A1 | 11/2006 | Subbu et al. |
| 2007/0061144 A1 | 3/2007 | Grichnik et al. |
| 2007/0094048 A1 | 4/2007 | Grichnik |
| 2007/0094181 A1 | 4/2007 | Tayebnejad et al. |
| 2007/0118338 A1 | 5/2007 | Grichnik et al. |
| 2007/0124237 A1 | 5/2007 | Sundararajan et al. |
| 2007/0150332 A1 | 6/2007 | Grichnik et al. |
| 2007/0168494 A1 | 7/2007 | Liu et al. |
| 2007/0179769 A1 | 8/2007 | Grichnik et al. |
| 2007/0203864 A1 | 8/2007 | Grichnik |
| 2008/0154811 A1 | 6/2008 | Grichnik et al. |

FOREIGN PATENT DOCUMENTS

| | | |
|---|---|---|
| EP | 1367248 | 12/2003 |
| EP | 1418481 | 5/2004 |
| JP | 10-332621 | 12/1998 |
| JP | 11-351045 | 12/1999 |
| JP | 2002-276344 | 9/2002 |
| WO | WO97/42581 | 11/1997 |

| | | |
|---|---|---|
| WO | WO02/057856 | 7/2002 |
| WO | WO2006/017453 | 2/2006 |

OTHER PUBLICATIONS

G. Galperin, G. Tesauro, Parallel Monte-Carlo Simulation of Neural Network Controllers, available at http://www-fp.mcs.anl.gov/ccst/research/reports_pre1998/neural_network/galperin.html, printed on Mar. 11, 2005.

U.S. Appl. No. 11/101,531 entitled "Process Model Monitoring Method and System," by Anthony J. grichnik et al., filed on Apr. 8, 2005.

U.S. Appl. No. 11/101,556 entitled "Mahalanobis Distance Genetic Algorithm (MDGA) Method and System," by Anthony Grichnik et al., filed on Apr. 8, 2005.

U.S. Appl. No. 11/101,554 entitled "Zeta Statistic Process Method and System," by Anthony Grichnik et al., filed on Apr. 8, 2005.

U.S. Appl. No. 11/101,532 entitled "Control System and Method," by Anthony Grichnik et al., filed on Apr. 8, 2005.

U.S. Appl. No. 11/101,544 entitled "Diagnostic and Prognostic Method and System," by Anthony Grichnik et al., filed on Apr. 8, 2005.

U.S. Appl. No. /101,498 entitled "Probabilistic Modeling System for Product Design," by Michael Seskin et al., filed on Apr. 8, 2005.

National Institute of Health, "10-year CVD Risk Calculator" available at http://hin.nhlbi.nih.gov/atpiii/calculator.asp?usertype=prof, printed on Aug. 5, 2005.

Allen et al., "Supersaturated Designs That Maximize the Probability of Identifying Active Factors," 2003 American Statistical Association and the American Society for Quality, Technometrics, vol. 45, No. 1, Feb. 2003, pp. 1-8.

April, Jay et al., "Practical Introduction to Simulation Optimization," Proceedings of the 2003 Winter Simulation Conference, pp. 71-78.

Bandte et al., "Viable Designs Through a Joint Probabilistic Estimation Technique," SAE International, and the American Institute of Aeronautics and Astronautics, Incl., Paper No. 1999-01-5623, 1999, pp. 1-11.

Beisl et al., "use of Genetic Algorithm to Identify the Source Point of Seepage Slick Clusters Interpreted from Radarsat-1 Images in the Gulf of Mexico," Geoscience and Remote Sensing Symposium, 2004, Proceedings, 2004 IEEE International Anchorage, AK, Sep. 20-24, 2004, vol. 6, Sep. 20, 2004, pp. 4139-4142.

Berke et al., "Optimum Design of Aerospace Structural Components Using Neural Networks," Computers and Structures, vol. 48, No. 6, Sep. 17, 1993, pp. 1001-1010.

Bezdek, "Genetic Algorithm Guided Clustering," IEEE 0-7803-1899-4/94, 1994, pp. 34-39.

Brahma et al., "Optimization of Diesel Engine Operating Parameters Using Neural Networks," SAE Technical Paper Series, 2003-01-3228, Oct. 27-30, 2003 (11 pages).

Chung et al., "Process Optimal Design in Forging by Genetic Algorithm," Journal of manufacturing Science and Engineering, vol. 124, May 2002, pp. 397-408.

Cox et al., "Statistical Modeling for Efficient Parametric Yield Estimation of MOS VLSI Circuits," IEEE, 1983, pp. 242-245.

De Maesschalck et al., "The Mahalanobis Distance," Chemometrics and Intelligent Laboratory Systems, vol. 50, No. 1, Jan. 2000, pp. 1-18.

Dikmen et al., "Estimating Distributions in Genetic Algorithms," ISCIS 2003, LNCS 2869, 2003, pp. 521-528.

Gletsos et al., "A Computer-Aided Diagnostic System to Characterize CT Focal Liver Lesions: Design and Optimization of a Neural network Classifier," IEEE Transactions on Information Technology in Biomedicine, vol. 7, No. 3, Sep. 2003 pp. 153-162.

Grichnik et al., "An Improved Metric for Robust Engineering," Proceedings of the 2007 International Conference on Scientific Computing, Las Vegas, NV (4 pages).

Grichnik et al., Copending U.S. Appl. No. 11/529,267, filed Sep. 29, 2006, entitled Virtual Sensor Based Engine Control System and Method.

Grichnik et al., Copending U.S. Appl. No. 11/730,363, filed Mar. 30, 2007, entitled Prediction Based Engine Control System and Method.

Grichnik et al., Copending U.S. Appl. No. 11/812,164, filed Jun. 15, 2007, entitled Virtual Sensor System and Method.

Grichnik et al., Copending U.S. Appl. No. 11/979,408, filed Nov. 2, 2007, entitled Virtual Sensor Network (VSN) System and Method.

Holland, John H., "Genetic Algorithms," Scientific American, Jul. 1992, pp. 66-72.

Hughes et al., "Linear Statistics for Zeros fo Riemann's Zeta Function," C.R. Acad. Sci. Paris, Ser. 1335 (2002), pp. 667-670.

Ko et al., "Application of Artificial Neural network and Taguchi Method to Perform Design in Metal Forming Considering Workability," International Journal of Machine Tools & Manufacture, vol. 39, No. 5, May 1999, pp. 771-785.

Kroha et al., "Object Server on a Parallel Computer," 1997 IEEE 0-8186-8147-0/97, pp. 284-288.

Mavris et al., "A Probabilistic Approach to Multivariate Constrained Robust Design Simulation," Society of Automotive Engineers, Inc., Paper No. 975508, 1997, pp. 1-11.

Obayashi et al, "Multiobjective Evolutionary Computation for Supersonic Wing-Shape Optimization," IEEE Transactions on Evolutionary Computation, vol. 4, No. 2, Jul. 2000, pp. 182-187.

Simpson et al., "Metamodels for Computer-Based Engineering Design: Survey & Recommendations," Engineering with Computers, 2001, vol. 17, pp. 129-150.

Solar Turbines, "InSight Systems, Machinery Management Solutions," Oct. 19, 2006.

Song et al., "The Hyperellipsoidal Clustering Using Genetic Algorithm," 1997 IEEE International Conference on Intelligent Processing Systems, Oct. 28-31, 1997, Beijing, China, pp. 592-596.

Taylor et al., "Guidelines for Evaluating and Expressing the Uncertainty of NIST Measurement Results," NIST Technical Note 1297, 1994 Edition, United States Dept. of Commerce, National Institute of Standards and Technology (25 pages).

Thompson, G.J. et al., "Neural Network Modelling of the Emissions and Performance of a Heavy-Duty Diesel Engine," Proc. Instu. Mech. Engrs., vol. 214, Part D (2000), pp. 111-126.

Traver, Michael L. et al., "Neural Network-Based Diesel Engine Emissions Prediction Using In-Cylinder Comustion Pressure," International Spring Fuels & Lubricants Meeting & Exposition, SAE Technical Paper Series, May 3-6, 1999, 17 pages.

Woodall, Tsui et al., "A Review and Analysis of the Mahalanobis-Taguchi Syste4m," technometrics, Feb. 2003, vol. 45, No. 1 (15 pages).

Wu et al., "Cam-phasing Optimization Using Artificial Neural Networks as Surrogate Models—Fuel Consumption and Nox Emissions," SAE Technical Paper Series, 2006-01-1512, Apr. 3-6, 2006 (19 pages).

Yang et al., "Similar Cases Retrieval from te Database of Laboratory Test Results," Journal of Medical Systems, vol. 27, No. 3, Jun. 2003, pp. 271-282.

Yuan et al., "Evolutionary Fuzzy C-Means Clustering Algorithm," 1995 IEEE 0-7803-2461-Jul. 1995, pp. 2221-2226.

Traver, Michael L. et al., "A Neural Network-Based Virtual NOx Sensor for Diesel Engines," West Virginia Univeristy, Mechanical and Aerospace Engineering Dept., Morgantown, WV 26506-6101, 6106, 7 pages.

\* cited by examiner

MEDICAL RISK STRATIFYING METHOD AND SYSTEM

TECHNICAL FIELD

This disclosure relates generally to computer based process modeling techniques and, more particularly, to methods and systems for stratifying medical risk using process models.

BACKGROUND

Medical-related information comes from many different sources, such as clinical data or non-clinical data. Medical-related information may be used by health care professionals for the prescription and analysis of tests and/or for the diagnosis and treatment of medical events. Medical-related information may also be used to analyze medical risks. Medical risk analysis may be an important tool to analyze the possibility of a certain type of medical risk based on certain types of medical-related information. For example, medical risk analysis may be used to analyze the possibility of lung disease based on whether or not a person is a smoker.

Process models and algorithms may be used to perform medical risk analysis. For example, U.S. Patent Application Publication No. 20040122703 to Walker et al. discloses a technique for developing a model of medical conditions and situations from medical data by using database techniques and neural network methods. However, such conventional techniques often fail to address inter-correlation between individual medical records, especially at the time of generation and/or optimization of process models, used for correlating medical information to medical risks.

Methods and systems consistent with certain features of the disclosed systems are directed to solving one or more of the problems set forth above.

SUMMARY OF THE INVENTION

One aspect of the present disclosure includes a method for a medical risk stratification system. The method may include establishing a medical risk process model indicative of interrelationships between a plurality of medical risks and a plurality of health parameters and obtaining a set of values corresponding to the plurality of health parameters. The method may also include calculating the values of the plurality of medical risks simultaneously based upon the set of values corresponding to the plurality of health parameters and the medical risk process model and presenting the values of the plurality of medical risks.

Another aspect of the present disclosure includes a computer system. The computer may include a database containing data records associating a plurality of medical risks and a plurality of health parameters and a processor. The processor may be configured to establish a medical risk process model indicative of interrelationships between the plurality of medical risks and the plurality of health parameters and to obtain a set of values corresponding to the plurality of health parameters. The processor may also be configured to calculate the values of the plurality of medical risks simultaneously based upon the set of values corresponding to the plurality of health parameters and the medical risk process model, to present the values of the plurality of medical risks, and to optimize the plurality of health parameters to minimize the plurality of medical risks simultaneously.

Another aspect of the present disclosure includes a computer-readable medium for use on a computer system configured to perform a medical risk stratification procedure. The computer-readable medium may have computer-executable instructions for performing a method. The method may include establishing a medical risk process model indicative of interrelationships between a plurality of medical risks and a plurality of health parameters and obtaining a set of values corresponding to the plurality of health parameters. The method may also include calculating the values of the plurality of medical risks simultaneously based upon the set of values corresponding to the plurality of health parameters and the medical risk process model and presenting the values of the plurality of medical risks.

DETAILED DESCRIPTION

Reference will now be made in detail to exemplary embodiments, which are illustrated in the accompanying drawings. Wherever possible, the same reference numbers will be used throughout the drawings to refer to the same or like parts.

Figure 1:
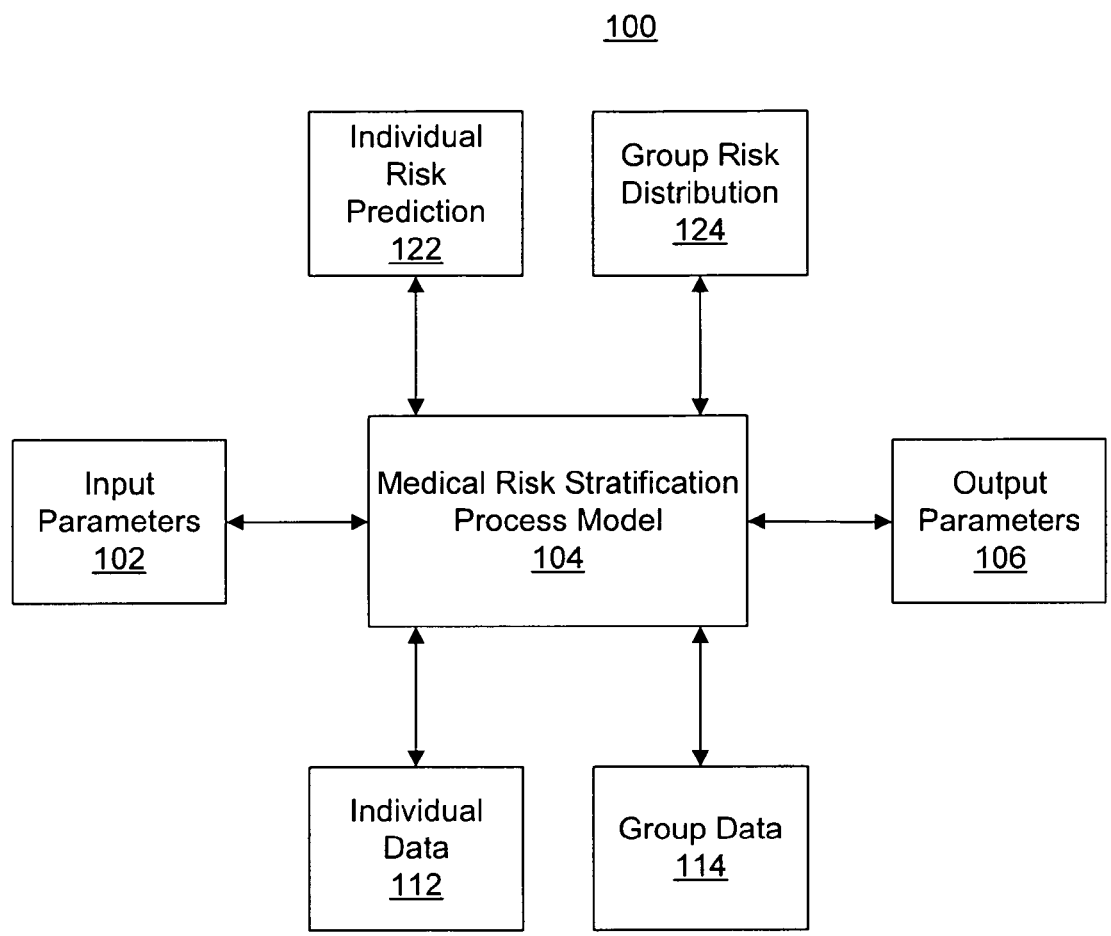
FIG. 1 is a pictorial illustration of an exemplary medical risk stratification process environment consistent with certain disclosed embodiments.

FIG. 1 illustrates a flowchart diagram of an exemplary medical risk stratification process modeling environment 100. As shown in FIG. 1, a medical risk stratification (MRS) process model 104 may be established to build interrelationships between input parameters 102 and output parameters 106. After MRS process model 104 is established, values of input parameters 102 may be provided to MRS process model 104 to predict values of output parameters 106 based on the given values of input parameters 102 and the interrelationships.

Input parameters 102 may include any appropriate type of data associated with a medical application. For example, input parameters 102 may include medical records from hospitals or other health institutions. Output parameters 106, on the other hand, may correspond to certain medical risks or any other types of output parameters used by the particular medical application.

MRS process model 104 may include any appropriate type of mathematical or physical model indicating interrelationships between input parameters 102 and output parameters 106. For example, MRS process model 104 may be a neural network based mathematical model that is trained to capture interrelationships between input parameters 102 and output parameters 106. Other types of mathematic models, such as fuzzy logic models, linear system models, and/or non-linear system models, etc., may also be used. MRS process model 104 may be trained and validated using data records collected from a particular application for which MRS process model 104 is established. That is, MRS process model 104 may be established according to particular rules corresponding to a particular type of model using the data records, and the interrelationships of MRS process model 104 may be verified by using part of the data records.

After MRS process model 104 is trained and validated, MRS process model 104 may be optimized to define a desired input space of input parameters 102 and/or a desired distribution of output parameters 106. The validated or optimized MRS process model 104 may used to produce corresponding values of output parameters 106 when provided with a set of values of input parameters 102. For example, MRS process model 104 may be used to produce individual risk prediction 122 based on individual data 112. Further, MRS process model 104 may also be used to find group risk prediction 124 based on group data 114.

Figure 2:
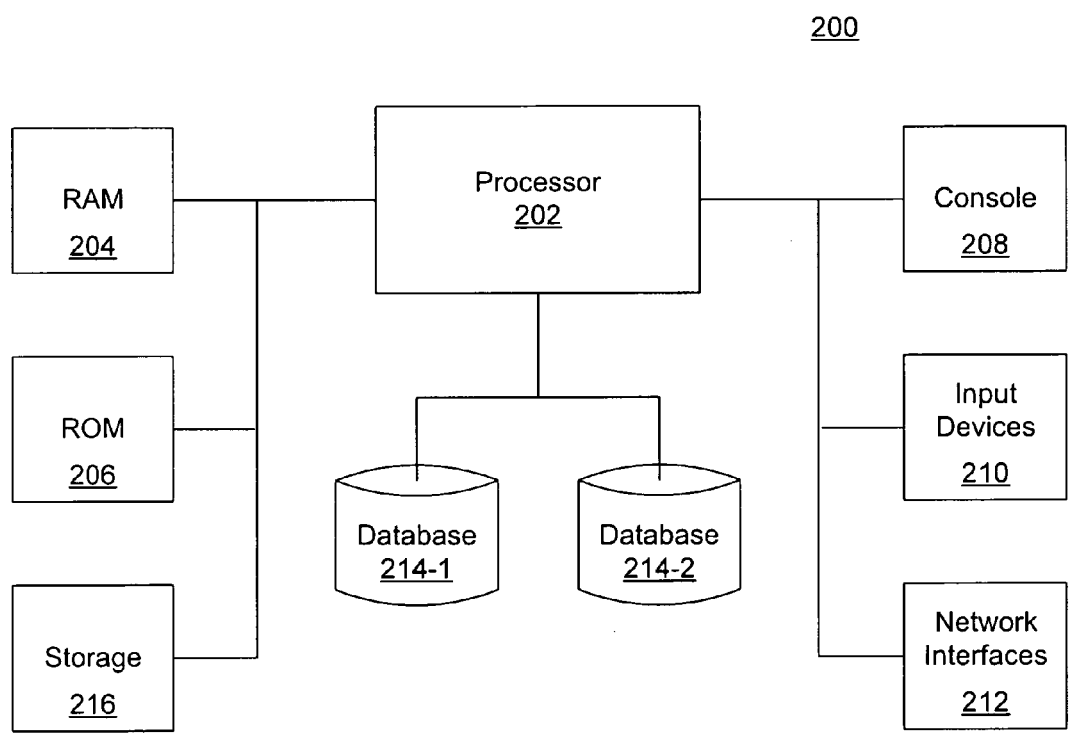
FIG. 2 illustrates a block diagram of a computer system consistent with certain disclosed embodiments.

The establishment and operations of MRS process model 104 may be carried out by one or more computer systems. FIG. 2 shows a functional block diagram of an exemplary computer system 200 that may be used to perform these modeling processes and operations.

As shown in FIG. 2, computer system 200 may include a processor 202, a random access memory (RAM) 204, a read-only memory (ROM) 206, a console 208, input devices 210, network interfaces 212, databases 214-1 and 214-2, and a storage 216. It is understood that the type and number of listed devices are exemplary only and not intended to be limiting. The number of listed devices may be changed and other devices may be added.

Processor 202 may include any appropriate type of general purpose microprocessor, digital signal processor, or microcontroller. Processor 202 may execute sequences of computer program instructions to perform various processes as explained above. The computer program instructions may be loaded into RAM 204 for execution by processor 202 from a read-only memory (ROM), or from storage 216. Storage 216 may include any appropriate type of mass storage provided to store any type of information that processor 202 may need to perform the processes. For example, storage 216 may include one or more hard disk devices, optical disk devices, or other storage devices to provide storage space.

Console 208 may provide a graphic user interface (GUI) to display information to users of computer system 200. Console 208 may include any appropriate type of computer display device or computer monitor. Input devices 210 may be provided for users to input information into computer system 200. Input devices 210 may include a keyboard, a mouse, or other optical or wireless computer input devices, etc. Further, network interfaces 212 may provide communication connections such that computer system 200 may be accessed remotely through computer networks via various communication protocols, such as transmission control protocol/internet protocol (TCP/IP), hyper text transfer protocol (HTTP), etc.

Databases 214-1 and 214-2 may contain model data and/or any information related to data records under analysis, such as training and testing data. Databases 214-1 and 214-2 may include any type of commercial or customized databases. Databases 214-1 and 214-2 may also include analysis tools for analyzing the information in the databases. Processor 202 may also use databases 214-1 and 214-2 to determine and store performance characteristics of MRS process model 104.

Figure 3:
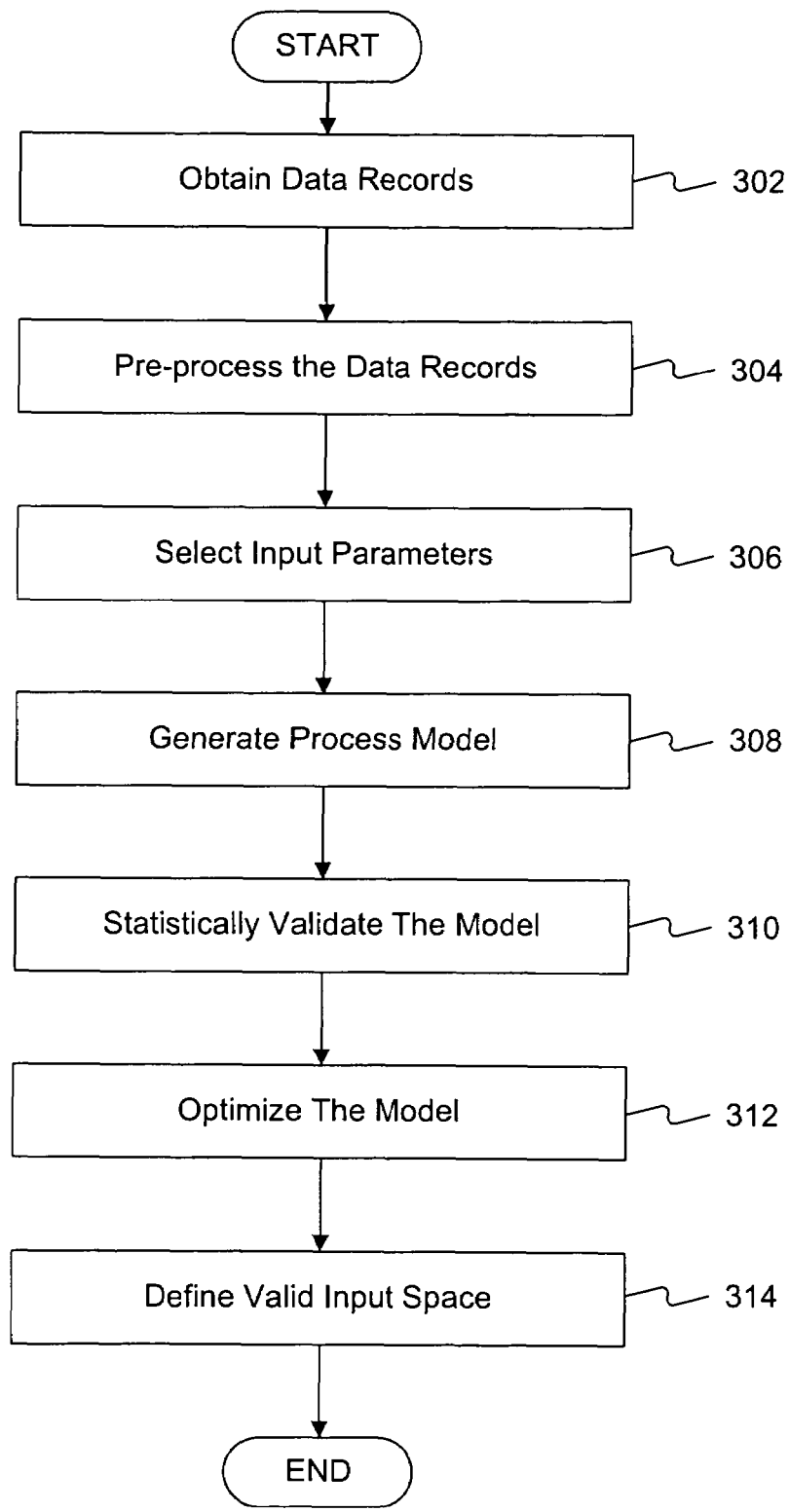
FIG. 3 illustrates a flowchart of an exemplary medical risk stratification model generation and optimization process consistent with certain disclosed embodiments.

Processor 202 may perform a medical risk stratification model generation and optimization process to generate and optimize MRS process model 104. FIG. 3 shows an exemplary model generation and optimization process performed by processor 202.

As shown in FIG. 3, at the beginning of the model generation and optimization process, processor 202 may obtain data records associated with input parameters 102 and output parameters 106 (step 302). The data records may include information characterizing individuals or a population, genetic information, medical events and states, treatments, diagnosis, and prognosis characterizations, etc. In particular, the data records may include demographic data (e.g., age, race, sex, work place, residence, life style, etc.), self-reported data (e.g., surveys captured intermittently from individuals or members of a population), prescription drug information (e.g., types and/or amount of prescription drugs taken by an individual or a population), diagnostic records (e.g., clinical tests and results), and treatment data (e.g., illness, treatment, hospital, and/or doctor, etc.).

For example, the data records may include information about parameters related to an individual patient's blood, urine, saliva and other fluid analysis (e.g., gastrointestinal, reproductive, and cerebrospinal fluid analysis). The data records may also include data obtained from various medical analysis systems, such as polymerase (PCR) chain reaction analysis systems, genetic marker analysis systems, radioimmunoassay systems, chromatography analysis systems, and/or receptor assay systems, etc. Data from other analysis systems, such as tissue analysis systems, cytology and tissue typing systems, and immunocytochemistry and histopathological analysis systems may also be included.

Further, the data records may include clinically measured information of individual patients, such as clinical medical data (e.g., age, sex, height, exercise level, cholesterol level, blood pressure, diet, particular diseases and treatments, health habit, etc.) or other clinical test data such as electroencephalographs (EEG), electrocardiographs (ECG), electromyographs (EMG), electrical impedance tomographs (EIT), nerve conduction test data, electronystagmographs (ENG), X-ray images, magnetic resonance (MR) images, computed tomography (CT) images, positron emission tomographs (PET), and/or flouorography, mammography, sonography, infrared, nuclear, and thermoacoustic images, etc.

The data records may also be collected from experiments designed for collecting such data. Alternatively, the data records may be generated artificially by other related processes, such as other medical modeling or analysis processes. The data records may also include training data used to build MRS process model 104 and testing data used to validate MRS process model 104. In addition, the data records may also include simulation data used to observe and optimize MRS process model 104.

The data records may reflect characteristics of input parameters 102 and output parameters 106, such as statistic distributions, normal ranges, and/or precision tolerances, etc. Once the data records are obtained (step 302), processor 202 may pre-process the data records to clean up the data records for obvious errors and to eliminate redundancies (step 304). Processor 202 may remove approximately identical data records and/or remove data records that are out of a reasonable range in order to be meaningful for model generation and optimization. After the data records have been pre-processed, processor 202 may select proper input parameters by analyzing the data records (step 306).

The data records may be associated with many input variables, such as variables corresponding to demographic data, self-reported data, prescription drug information, diagnostic records, and treatment data, etc. The number of input variables may be greater than the number of input parameters 102 used for MRS process model 104, that is, input parameters 102 may be a subset of the input variables. For example, the data records may be associated with several medical conditions, such as lung, liver, heart, and/or other organs; while input parameters 102 of a particular process, such as Cardiovascular disease (CVD), may only include heart related information and/or information on blood pressure, cholesterol level, and/or lifestyle, etc.

In certain situations, the number of input variables in the data records may exceed the number of the data records and lead to sparse data scenarios. Some of the extra input variables may have to be omitted in certain mathematical models. The number of the input variables may need to be reduced to create mathematical models within practical computational time limits.

Processor 202 may select input parameters 102 according to predetermined criteria. For example, processor 202 may choose input parameters 102 by experimentation and/or expert opinions. Alternatively, in certain embodiments, processor 202 may select input parameters based on a mahalanobis distance between a normal data set and an abnormal data set of the data records. The normal data set and abnormal data set may be defined by processor 202 using any appropriate method. For example, the normal data set may include characteristic data associated with input parameters 102 that produce desired output parameters. On the other hand, the abnormal data set may include any characteristic data that may be out of tolerance or may need to be avoided. The normal data set and abnormal data set may be predefined by processor 202.

Mahalanobis distance may refer to a mathematical representation that may be used to measure data profiles based on correlations between parameters in a data set. Mahalanobis distance differs from Euclidean distance in that mahalanobis distance takes into account the correlations of the data set. Mahalanobis distance of a data set X (e.g., a multivariate vector) may be represented as $$MD_i = (X_i - \mu_x)\Sigma^{-1}(X_i - \mu_x)' \quad (1)$$

where $\mu_x$ is the mean of X and $\Sigma^{-1}$ is an inverse variance-covariance matrix of X. $MD_i$ weights the distance of a data point $X_i$ from its mean $\mu_x$ such that observations that are on the same multivariate normal density contour will have the same distance. Such observations may be used to identify and select correlated parameters from separate data groups having different variances.

Processor 202 may select a desired subset of input parameters such that the mahalanobis distance between the normal data set and the abnormal data set is maximized or optimized. A genetic algorithm may be used by processor 202 to search input parameters 102 for the desired subset with the purpose of maximizing the mahalanobis distance. Processor 202 may select a candidate subset of input parameters 102 based on a predetermined criteria and calculate a mahalanobis distance $MD_{normal}$ of the normal data set and a mahalanobis distance $MD_{abnormal}$ of the abnormal data set. Processor 202 may also calculate the mahalanobis distance between the normal data set and the abnormal data (i.e., the deviation of the mahalanobis distance $MD_x = MD_{normal} - MD_{abnormal}$). Other types of deviations, however, may also be used.

Processor 202 may select the candidate subset of input variables 102 if the genetic algorithm converges (i.e., the genetic algorithm finds the maximized or optimized mahalanobis distance between the normal data set and the abnormal data set corresponding to the candidate subset). If the genetic algorithm does not converge, a different candidate subset of input variables may be created for further searching. This searching process may continue until the genetic algorithm converges and a desired subset of input variables (e.g., input parameters 102) is selected.

After selecting input parameters 102 (e.g., age, sex, height, exercise level, cholesterol level, blood pressure, diet, particular diseases and treatments, health habit, etc.), processor 202 may generate MRS process model 104 to build interrelationships between input parameters 102 and output parameters 106 (step 308). In certain embodiments, MRS process model 104 may correspond to a computational model, such as, for example, a computational model built on any appropriate type of neural network. The type of neural network computational model that may be used may include back propagation, feed forward models, cascaded neural networks, and/or hybrid neural networks, etc. Particular type or structures of the neural network used may depend on particular applications. Other types of computational models, such as linear system or non-linear system models, etc., may also be used.

The neural network computational model (i.e., MRS process model 104) may be trained by using selected data records. For example, the neural network computational model may include a relationship between output parameters 106 (e.g., medical risks, etc.) and input parameters 102 (e.g., age, sex, weight, height, exercise level, cholesterol level, blood pressure, diet, habit, etc.). The neural network computational model may be evaluated by predetermined criteria to determine whether the training is completed. The criteria may include desired ranges of accuracy, time, and/or number of training iterations, etc.

After the neural network has been trained (i.e., the computational model has initially been established based on the predetermined criteria), processor 202 may statistically validate the computational model (step 310). Statistical validation may refer to an analyzing process to compare outputs of the neural network computational model with actual or expected outputs to determine the accuracy of the computational model. Part of the data records may be reserved for use in the validation process.

Alternatively, processor 202 may also generate simulation or validation data for use in the validation process. This may be performed either independently of a validation sample or in conjunction with the sample. Statistical distributions of inputs may be determined from the data records used for modeling. A statistical simulation, such as Latin Hypercube simulation, may be used to generate hypothetical input data records. These input data records are processed by the computational model, resulting in one or more distributions of output characteristics. The distributions of the output characteristics from the computational model may be compared to distributions of output characteristics observed in a population. Statistical quality tests may be performed on the output distributions of the computational model and the observed output distributions to ensure model integrity.

Once trained and validated, MRS process model 104 may be used to predict values of output parameters 106 when provided with values of input parameters 102. Further, processor 202 may optimize MRS process model 104 by determining desired distributions of input parameters 102 based on relationships between input parameters 102 and desired distributions of output parameters 106 (step 312).

Processor 202 may analyze the relationships between desired distributions of input parameters 102 and desired distributions of output parameters 106 based on particular applications. For example, processor 202 may select desired ranges for output parameters 106 (e.g., likelihood of cardiovascular disease, diabetics, and/or high blood pressure, etc.). Processor 202 may then run a simulation of the computational model to find a desired statistic distribution for an individual input parameter (e.g., age, sex, weight, height, exercise level, cholesterol level, blood pressure, diet, habit, etc.). That is, processor 202 may separately determine a distribution (e.g., mean, standard variation, etc.) of the individual input parameter corresponding to the normal ranges of output parameters 106. After determining respective distributions for all individual input parameters, processor 202 may combine the desired distributions for all the individual input parameters to determine desired distributions and characteristics for overall input parameters 102.

Alternatively, processor 202 may identify desired distributions of input parameters 102 simultaneously to maximize the possibility of obtaining desired outcomes. In certain embodiments, processor 202 may simultaneously determine desired distributions of input parameters 102 based on zeta statistic. Zeta statistic may indicate a relationship between input parameters, their value ranges, and desired outcomes. Zeta statistic may be represented as $$\zeta = \sum_{1}^{j} \sum_{1}^{i} |S_{ij}| \left(\frac{\sigma_i}{\bar{x}_i}\right)\left(\frac{\bar{x}_j}{\sigma_j}\right),$$

where $\bar{x}_i$ represents the mean or expected value of an ith input; $\bar{x}_j$ represents the mean or expected value of a jth outcome; $\sigma_i$ represents the standard deviation of the ith input; $\sigma_j$ represents the standard deviation of the jth outcome; and $|S_{ij}|$ represents the partial derivative or sensitivity of the jth outcome to the ith input.

Under certain circumstances, $\bar{x}_i$ may be less than or equal to zero. A value of $3\sigma_i$ may be added to $\bar{x}_i$ to correct such problematic condition. If, however, $\bar{x}_i$ is still equal zero even after adding the value of $3\sigma_i$, processor 202 may determine that $\sigma_i$ may be also zero and that the process model under optimization may be undesired. In certain embodiments, processor 202 may set a minimum threshold for $\sigma_i$ to ensure reliability of process models. Under certain other circumstances, $\sigma_j$ may be equal to zero. Processor 202 may then determine that the model under optimization may be insufficient to reflect output parameters within a certain range of uncertainty. Processor 202 may assign an indefinite large number to $\zeta$.

Processor 202 may identify a desired distribution of input parameters 102 such that the zeta statistic of the neural network computational model (i.e., MRS process model 104) is maximized or optimized. An appropriate type of genetic algorithm may be used by processor 202 to search the desired distribution of input parameters with the purpose of maximizing the zeta statistic. Processor 202 may select a candidate set of input parameters 102 with predetermined search ranges and run a simulation of MRS process model 104 to calculate the zeta statistic parameters based on input parameters 102, output parameters 106, and the neural network computational model. Processor 202 may obtain $\bar{x}_i$ and $\sigma_i$ by analyzing the candidate set of input parameters 102, and obtain $\bar{x}_j$ and $\sigma_j$ by analyzing the outcomes of the simulation. Further, processor 202 may obtain $|S_{ij}|$ from the trained neural network as an indication of the impact of the ith input on the jth outcome.

Processor 202 may select the candidate set of input parameters if the genetic algorithm converges (i.e., the genetic algorithm finds the maximized or optimized zeta statistic of MRS process model 104 corresponding to the candidate set of input parameters). If the genetic algorithm does not converge, a different candidate set of input parameters 102 may be created by the genetic algorithm for further searching. This searching process may continue until the genetic algorithm converges and a desired set of input parameters 102 is identified. Processor 202 may further determine desired distributions (e.g., mean and standard deviations) of input parameters 102 based on the desired input parameter set. Once the desired distributions are determined, processor 202 may define a valid input space that may include any input parameter within the desired distributions (step 314).

In one embodiment, statistical distributions of certain input parameters may be impossible or impractical to control. For example, an input parameter may be associated with a physical attribute of a patient, such as age, or the input parameter may be associated with a constant variable within MRS process model 104 itself. These input parameters may be used in the zeta statistic calculations to search or identify desired distributions for other input parameters corresponding to constant values and/or statistical distributions of these input parameters.

Figure 4:
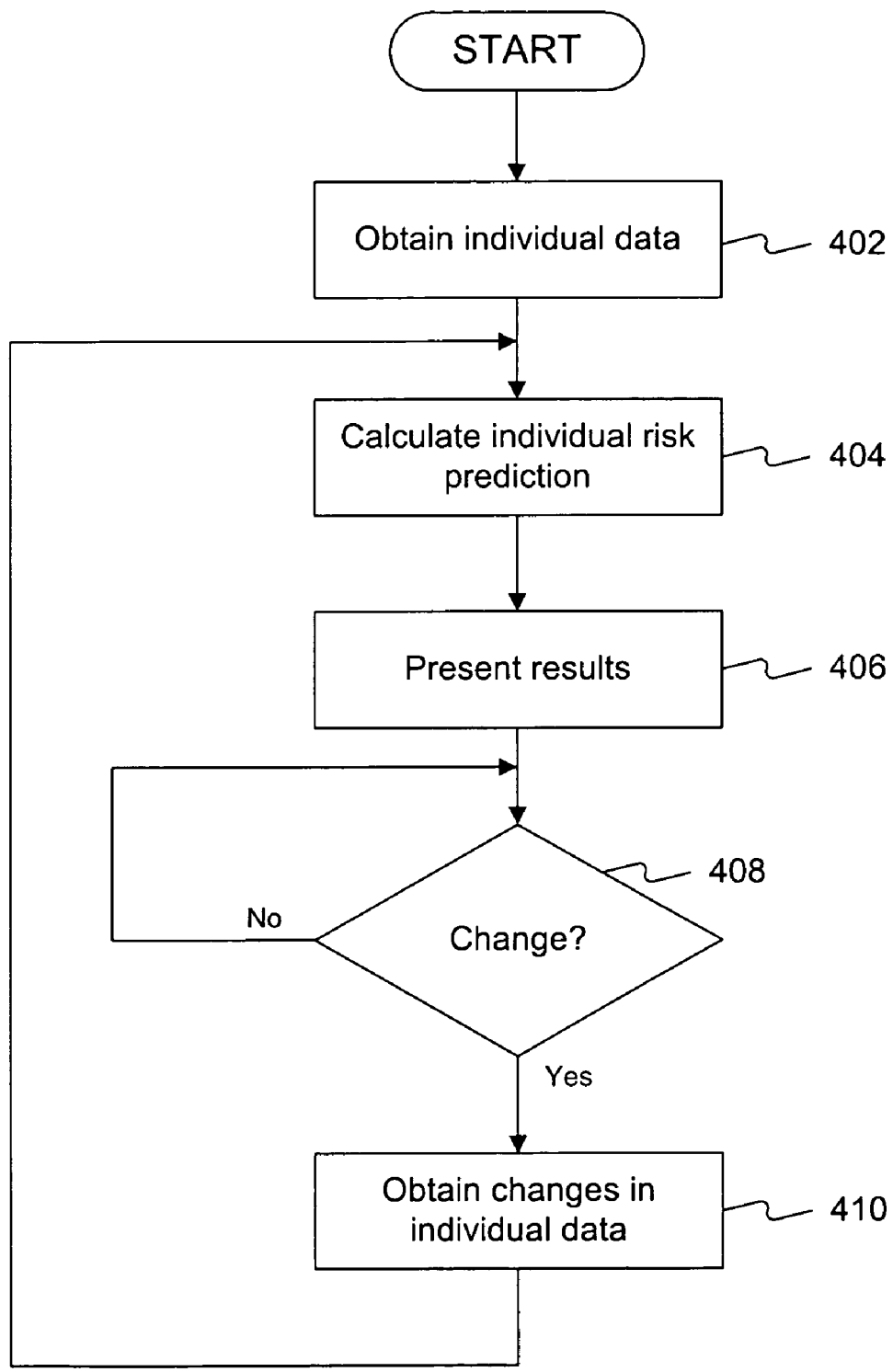
FIG. 4 shows an exemplary individual perspective process consistent with certain disclosed embodiments.

Returning to FIG. 1, after MRS process model 104 is trained, validated, and optimized, an individual user may use MRS process model to predict one or more medical risks based upon individual medical data. Processor 202 may perform an individual perspective process to provide information on medical risks to the individual user. For example, processor 202 may provide individual risk prediction 122 based on MRS process model 104 and individual data 112. FIG. 4 shows an exemplary individual perspective process performed by processor 202.

Processor 202 may obtain individual data 112 from the individual user (step 402). Processor 202 may obtain individual data 112 directly from user inputs, from a database, or from other computer systems maintaining such data. Individual data 112 may reflect any health related information about the individual user, such as age, sex, height, exercise level, cholesterol level, blood pressure, diet, particular diseases and treatments, health habit (e.g., smoking, alcohol), etc.

After obtaining individual data 112, processor 202 may calculate individual risk predication 122 based on MRS process model 104 (step 404). For example, processor 202 may calculate medical risks such as cardiovascular disease, diabetic, etc., based on input individual data 112 (e.g., age, sex, height, exercise level, cholesterol level, blood pressure, diet, particular diseases and treatments, health habit, etc.) and MRS process model 104. Processor 202 may also calculate certain other calculations related to individual data 112 and individual risk prediction 122, such as statistics about individual data 112 in comparison with input parameters 102.

Figure 5:
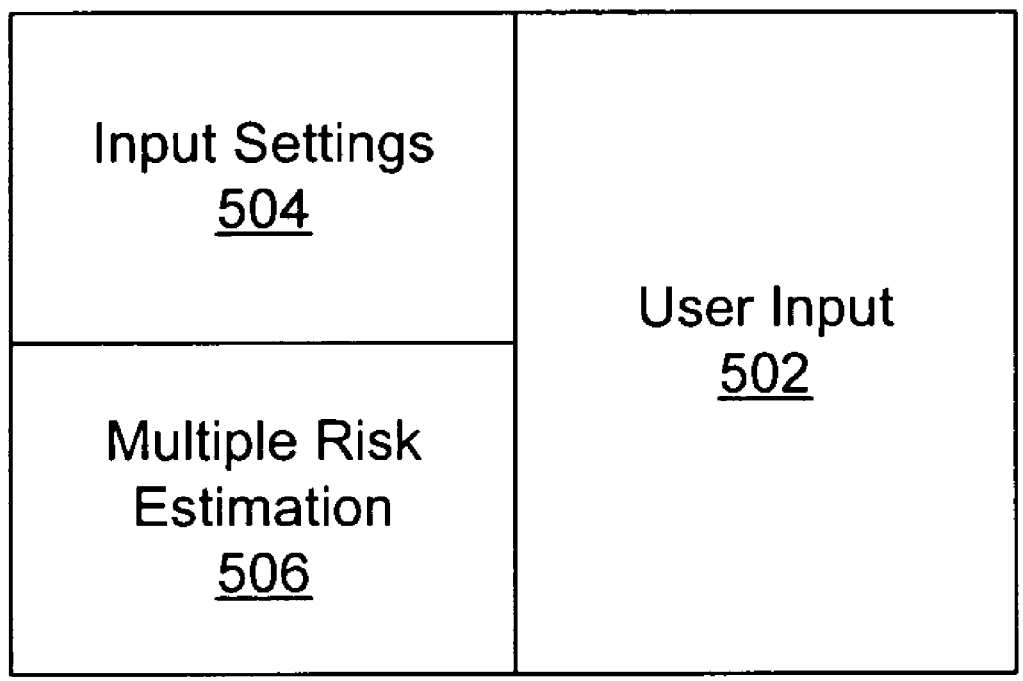
FIG. 5 shows a block diagram of an exemplary graphical user interface consistent with certain disclosed embodiments.

Processor 202 may also present individual risk prediction 122 and results of other calculation to the individual user through a user interface (step 406). The user interface may include any appropriate textual, audio, and/or visual user interface. FIG. 5 shows a block diagram of an exemplary graphical user interface (GUI) 500 on console 208.

As shown in FIG. 5, GUI 500 may include separate display areas to present different types of data. For example, GUI 500 may include a user input area 502, an input setting area 504, and a multiple risk estimation area 506. Other display areas, however, may also be used. User input area 502 may be used to accept health data input (i.e., individual data 112) from the individual user and/or to allow the user to change the values of certain inputs to observe the likely effect of such changes. In certain embodiments, slider control mechanism may be used such that the user may easily set or change the inputs. In addition, the slider control may also be used to set minimum and maximum limits for such inputs. These limits may be pre-determined or may be determined at real-time by MRS process model 104.

Input setting area 504 may be used to list values of input data 112 (e.g., such as age, sex, height, exercise level, cholesterol level, blood pressure, diet, particular diseases and treatments, and health habit, etc.). Input setting area may also show a comparison between values of individual data 112 with the overall values of input parameters 102 that are used to generate MRS process model 104. Further, multiple risk estimation area 506 may be used to present to the user how multiple risk may be related to one or more health input data. For example, multiple risk estimation area 506 may include a radar control chart to show how a particular set of inputs drive the values of multiple health risks.

Returning to FIG. 4, after processor 202 calculates individual risk prediction 122 and presents the calculation and certain other data to the user (steps 404 and 406), processor 202 may determine whether there are any changes on the values of individual data 112 (step 408). If there is no change (step 408; no), processor 202 may continue step 408 to monitor any change that may be made by the user. On the other hand, if any of individual data 112 has been changed (step 408; yes), processor 202 may obtain changed individual data 112 (step 410). Further, the individual perspective process may be continued at step 404 to calculate individual predication 122 based on the changed individual data 112.

Figure 6:
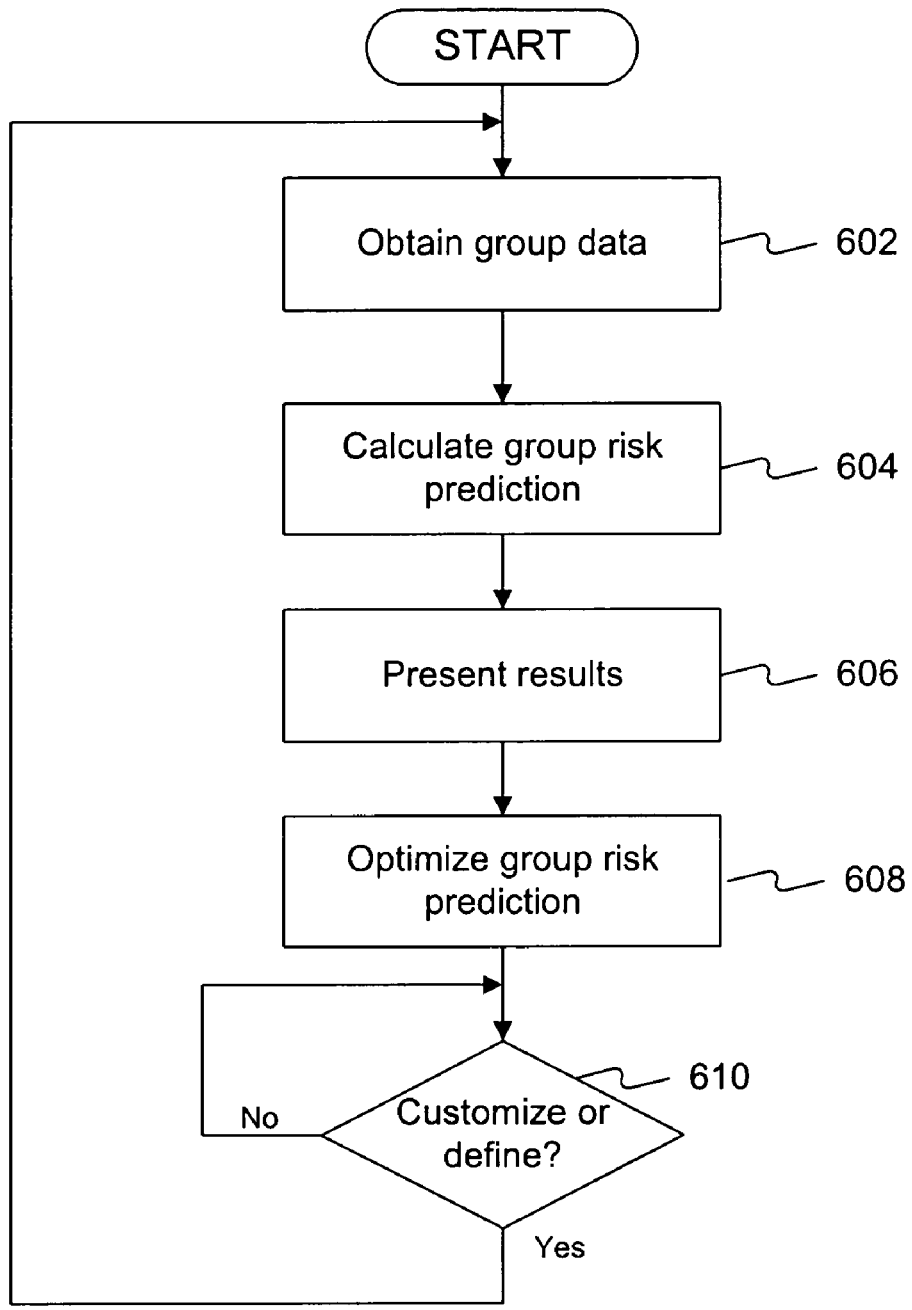
FIG. 6 shows an exemplary group perspective process consistent with certain disclosed embodiments.

Additionally or alternatively, a healthcare institution or other organizations may also use MRS process model 104 to manage health care risks and/or to profile health habits of a particular population. Process 202 may perform a group perspective process to identify medical risks and their corresponding mitigation factors. For example, processor 202 may provide group risk prediction 124 based on MRS process model 104 and group data 114. FIG. 6 shows an exemplary group perspective process.

As shown in FIG. 6, processor 202 may obtain group data 114 (step 602). Processor 202 may obtain group data 114 directly from input devices 210 under the control of an administrator of computer system 200. Alternatively, processor 202 may also obtain group data 114 from a database (e.g., database 214-1, database 214-2, etc.) or from other computer systems maintaining such data. Group data 114 may reflect health related information about a particular group or population. Such health related information may include age, sex, height, exercise level, cholesterol level, blood pressure, diet, particular diseases and treatments, health habit (e.g., smoking, alcohol), etc. Further, group data 114 may include historical health data and/or user-defined health data.

After obtaining group data 114, processor 202 may calculate group risk predication 124 based on MRS process model 104 (step 604). For example, processor 202 may calculate health risks for a particular group, such as cardiovascular disease, diabetic, etc., based on group data 114 and MRS process model 104. Processor 202 may also calculate distribution data of the health risks based on group data 114 and group risk prediction 124. For example, processor 202 may calculate likelihood of a certain disease among different age group or ethnic groups. Other statistics of group data 114 and group risk prediction 124 may also be calculated. Processor 202 may also optimize (e.g., to minimize the overall health risks) group risk prediction 124 based on desired distributions of group data 114, such as desired exercise level, diet, treatments, and/or health habit, etc. Processor 202 may optimize group risk prediction 124 based on zeta statistic, as explained in above sections. A new set of values of group data 114 (i.e., optimized group data 114) may be identified to minimize a certain type of health risk. Other optimization methods, however, may also be used. For example, the administrator may define a set of values of group data 114 (i.e., user-defined group data 114) based on predetermined criteria to minimize one or more health risks.

Figure 7:
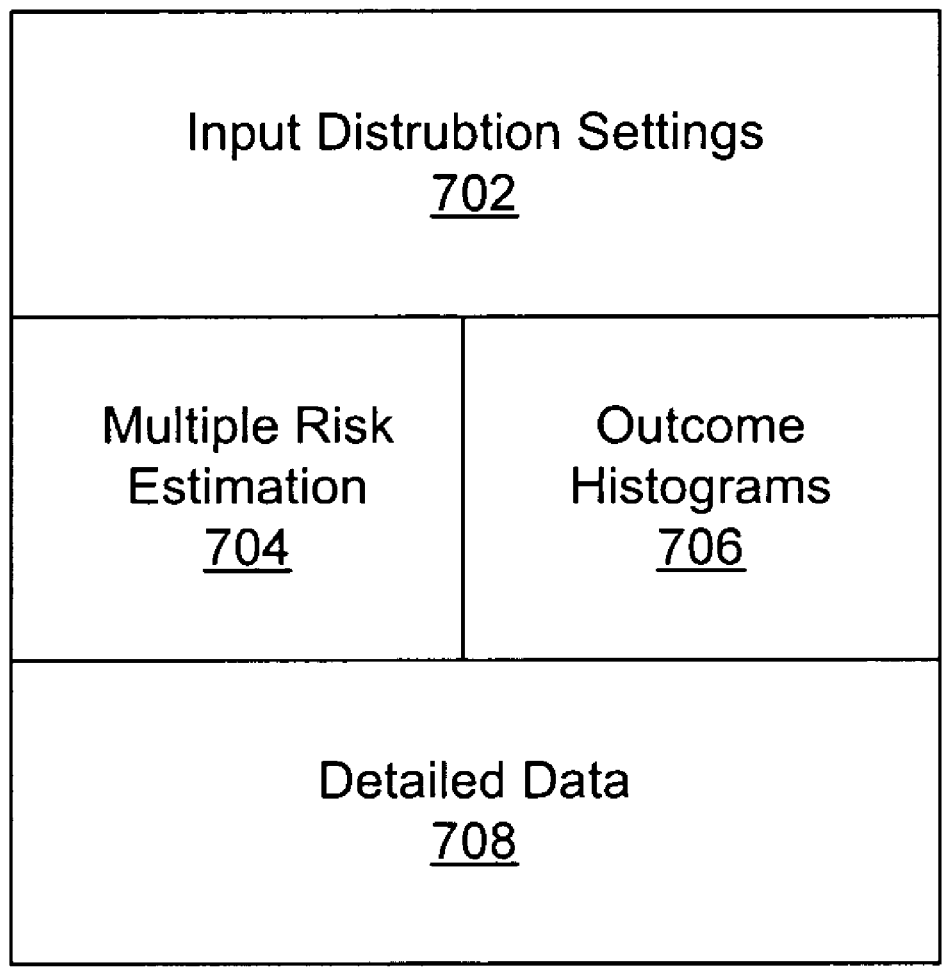
FIG. 7 shows another block diagram of an exemplary graphical user interface consistent with certain disclosed embodiments.

Processor 202 may also present the results of the group perspective process to the administrator through a user interface (step 606). Similar to the user interface provided for the individual perspective process, the user interface for group perspective process may include any appropriate user interface, such as textual (e.g., electronic mail), audio, or visual interfaces, or any combination thereof. FIG. 7 shows an exemplary graphical user interface (GUI) 700 provided on console 208.

GUI 700 may also include separate display areas to present different types of data. For example, GUI 700 may include an input data distribution settings area 702, a multiple risk estimation area 704, an outcome histogram area 706, and a detailed data area 708. Other display areas, however, may also be used.

Input data distribution settings area 702 may be used to display original group data 114, optimized group data 114, and/or user-defined group data 114. These group data (e.g., different distributions of group health information among a group or population) may also be displayed simultaneously to provide comparisons among different group data.

Multiple risk estimation area 704 may be used to display how multiple risks may be related to one or more health input data from group data 114. For example, multiple risk estimation area 704 may include a radar control chart to show how a particular set of group data drive the likelihood of multiple health risks. Further, outcome histogram area 706 may be used to show different values of group risk predication 124 respectively corresponding to original group data 114, optimized group data 114, and/or user-defined group data 114.

Detailed data area 708 may be used to display values of various data used in the group perspective process performed by processor 202, such as a spread sheet showing detailed data in calculations corresponding to group risk predication and/or optimization of group data 114, etc.

Returning to FIG. 6, processor 202 may optimize multiple health risks of group risk prediction 124 (step 608). For example, processor 202 may minimize the multiple health risks by calculating a desired set of values of group data 114. Zeta statistic may also be used in the optimization.

After processor 202 presents the results of the calculation (step 606) and the optimization (step 608), processor 202 may determine whether the administrator wants to customize or define group data 114 (step 610). If customization is not needed (step 610; no), processor 202 may continue step 610 to monitor any change that may be made by the administrator. On the other hand, if customization is needed (step 610; yes), processor 202 may proceed to step 602 to obtain changed group data 114 and continue the group perspective process.

INDUSTRIAL APPLICABILITY

The disclosed systems and methods may provide efficient and accurate medical risk stratification based on health information such as genetic, lifestyle, and/or environmental factors (both current and historical). Such technology may be used to predict and manage individual health risks as well as to analyze and manage health risks of a group or a population.

Individual users may use the disclosed systems and methods to predict potential health risks or to calculate likelihood of a possible disease based on their own health data. The individual users may also reduce the risks or the likelihood of a disease by changing relevant health data (e.g., lifestyle) corresponding to the risks or the disease.

Group or institutional users may use the disclosed systems and methods to calculate health risks among a population, such as a particular distribution among the population. The institutional users may also optimize the distribution to reduce the health risks of a population and to promote healthy lifestyle.

The disclosed systems and methods may also be extended to be used in non-medical field to predict or optimize other risks, such as financial market, etc. Parts of the disclosed system or steps of the disclosed method may be used by computer system providers to facilitate or integrate other process models.

Other embodiments, features, aspects, and principles of the disclosed exemplary systems will be apparent to those skilled in the art and may be implemented in various environments and systems.

What is claimed is:

1. A computer-implemented method for a medical risk stratification system, comprising:
   establishing a medical risk process model indicative of interrelationships between a plurality of medical risks and a plurality of health parameters;
   obtaining a set of values corresponding to the plurality of health parameters;
   calculating the values of the plurality of medical risks simultaneously based upon the set of values corresponding to the plurality of health parameters and the medical risk process model;
   presenting the values of the plurality of medical risks;
   optimizing the plurality of health parameters to minimize the plurality of medical risks simultaneously based upon at least desired values of the plurality of medical risks and sensitivity of the plurality of medical risks to the plurality of health parameters using a zeta statistic measure; and
   re-presenting the values of the plurality of medical risks.

2. The computer-implemented method according to claim 1, wherein the establishing includes:
   obtaining data records associated with a plurality of health variables and the plurality of medical risks;
   selecting the plurality of health parameters from the plurality of health variables, wherein a total number of the plurality of health parameters is less than a total number of the plurality of health variables; and
   generating the medical risk process model indicative of the interrelationships; and
   the optimizing includes:
   determining desired statistical distributions of the plurality of health parameters of the medical risk process model based upon at least the desired values of the plurality of medical risks and the sensitivity of the plurality of medical risks to the plurality of health parameters using the zeta statistic measure; and
   recalibrating the plurality of health parameters based on the desired statistical distributions.

3. The computer-implemented method according to claim 2, wherein selecting further includes:
   pre-processing the data records; and
   using a genetic algorithm to select the plurality of health parameters from the plurality of health variables based on a mahalanobis distance between a normal data set and an abnormal data set of the data records.

4. The computer-implemented method according to claim 2, wherein generating further includes:
   creating the medical risk process model as a neural network computational model;
   training the neural network computational model using the data records; and
   validating the neural network computation model using the data records.

5. The computer-implemented method according to claim 2, wherein determining further includes:
   determining a candidate set of the health parameters with a maximum zeta statistic using a genetic algorithm; and
   determining the desired distributions of the health parameters based on the candidate set,
   wherein the zeta statistic ζ is represented by:

$$\zeta = \sum_{1}^{j} \sum_{1}^{i} |S_{ij}| \left(\frac{\sigma_i}{\bar{x}_i}\right)\left(\frac{\bar{x}_j}{\sigma_j}\right),$$

provided that $\bar{x}_i$ represents a mean of an ith input; $\bar{x}_j$ represents a mean of a jth output; $\sigma_i$ represents a standard deviation of the ith input; $\sigma_j$ represents a standard deviation of the jth output; and $|S_{ij}|$ represents sensitivity of the jth output to the ith input of the medical risk process model.

6. The computer-implemented method according to claim 1, wherein the obtaining includes:
   obtaining, from an individual user of the medical risk stratification system, the set of values indicative of health information about the individual user.

7. The computer-implemented method according to claim 1, wherein the obtaining includes:
   obtaining the set of values indicative of health information about a population.

8. The computer-implemented method according to claim 1, wherein the presenting includes:
   presenting the set of values of the plurality of health parameters in a first display area;
   presenting statistic data corresponding to the plurality of heath parameters in a second display area; and
   presenting the interrelationships between the plurality of health parameters and the plurality of medical risks in a third display area.

9. The computer-implemented method according to claim 8, further includes:
   presenting detailed data associated with the medical risk process model in a fourth display area.

10. A computer system, comprising:
    a database containing data records associating a plurality of medical risks and a plurality of health parameters; and
    a processor that performs:
    establishing a medical risk process model indicative of interrelationships between the plurality of medical risks and the plurality of health parameters;
    obtaining a set of values corresponding to the plurality of health parameters;

calculating the values of the plurality of medical risks simultaneously based upon the set of values corresponding to the plurality of health parameters and the medical risk process model;

presenting the values of the plurality of medical risks;

optimizing the plurality of health parameters to minimize the plurality of medical risks simultaneously based upon at least desired values of the plurality of medical risks and sensitivity of the plurality of medical risks to the plurality of health parameters using a zeta statistic measure; and re-presenting the values of the plurality of medical risks.

11. The computer system according to claim 10, wherein establishing the medical risk process model further includes:

obtaining data records associated with a plurality of health variables and the plurality of medical risks;

selecting the plurality of health parameters from the plurality of health variables, wherein a total number of the plurality of health parameters is less than a total number of the plurality of health variables; and generating the medical risk process model indicative of the interrelationships; and optimizing the plurality of health parameters further includes:

determining desired statistical distributions of the plurality of health parameters of the medical risk process model based upon at least the desired values of the plurality of medical risks and the sensitivity of the plurality of medical risks to the plurality of health parameters using the zeta statistic measure; and recalibrating the plurality of health parameters based on the desired statistical distributions.

12. The computer system according, to claim 11, wherein selecting the plurality of health parameters further includes:

pre-processing the data records; and using a genetic algorithm to select the plurality of health parameters from the plurality of health variables based on a mahalanobis distance between a normal data set and an abnormal data set of the data records.

13. The computer system according to claim 11, wherein generating the medical risk process model further includes:

creating the medical risk process model as a neural network computational model;

training the neural network computational model using the data records; and validating the neural network computation model using the data records.

14. The computer system according to claim 11, wherein determine the respective desired statistical distributions further includes determine a candidate set of the health parameters with a maximum zeta statistic using a genetic algorithm; and determine the desired distributions of the health parameters based on the candidate set, wherein the zeta statistic $\zeta$ is represented by:

$$\zeta = \sum_{1}^{j} \sum_{1}^{i} |S_{ij}| \left(\frac{\sigma_i}{\bar{x}_i}\right)\left(\frac{\bar{x}_j}{\sigma_j}\right),$$

provided that $\bar{x}_i$ represents a mean of an ith input; $\bar{x}_j$ represents a mean of a jth output; $\sigma_i$ represents a standard deviation of the ith input; $\sigma_j$ represents a standard deviation of the jth output; and $|S_{ij}|$ represents sensitivity of the jth output to the ith input of the medical risk process model.

15. The computer system according to claim 10, further including:

one or more input devices that obtains the set of values corresponding to the plurality of health parameters indicative of health information about an individual user or a population.

16. The computer system according to claim 10, further including:

a display device that performs:

displaying a set of values of the plurality of health parameters in a first display area;

displaying statistic data corresponding to the plurality of health parameters in a second display area; and displaying the interrelationships between the plurality of health parameters and the plurality of medical risks in a third display area.

17. A computer-readable medium for use on a computer system that performs a medical risk stratification procedure, the computer-readable medium having computer-executable instructions for performing a method comprising:

establishing a medical risk process model indicative of interrelationships between a plurality of medical risks and a plurality of health parameters;

obtaining a set of values corresponding to the plurality of health parameters;

calculating the values of the plurality of medical risks simultaneously based upon the set of values corresponding to the plurality of health parameters and the medical risk process model;

presenting the values of the plurality of medical risks;

optimizing the plurality of health parameters to minimize the plurality of medical risks simultaneously based upon at least desired values of the plurality of medical risks and sensitivity of the plurality of medical risks to the plurality of health parameters using a zeta statistic measure; and re-presenting the values of the plurality of medical risks.

18. The computer-readable medium according to claim 17, wherein the establishing includes:

obtaining data records associated with a plurality of health variables and the plurality of medical risks;

selecting the plurality of health parameters from the plurality of health variables, wherein a total number of the plurality of health parameters is less than a total number of the plurality of health variables; and generating medical risk process model indicative of the interrelationships; and the optimizing includes:

determining desired statistical distributions of the plurality of health parameters of the medical risk process model based upon at least the desired values of the plurality of medical risks and the sensitivity of the plurality of medical risks to the plurality of health parameters using a zeta statistic measure; and recalibrating the plurality of health parameters based on the desired statistical distributions.

19. The computer-readable medium according to claim 18, wherein selecting further includes:

pre-processing the data records; and using a genetic algorithm to select the plurality of health parameters from the plurality of health variables based on a mahalanobis distance between a normal data set and an abnormal data set of the data records.

20. The computer-readable medium according to claim 18, wherein generating further includes:
   creating the medical risk process model as a neural network computational model;
   training the neural network computational model using the data records; and
   validating the neural network computation model using the data records.

21. The computer-readable medium according to claim 18, wherein determining further includes:
   determining a candidate set of the health parameters with a maximum zeta statistic using a genetic algorithm; and
   determining the desired distributions of the health parameters based on the candidate set,
   wherein the zeta statistic $\zeta$ is represented by:

$$\zeta = \sum_1^j \sum_1^i |S_{ij}| \left(\frac{\sigma_i}{\bar{x}_i}\right)\left(\frac{\bar{x}_j}{\sigma_j}\right),$$

provided that $\bar{x}_i$ represents a mean of an ith input; $\bar{x}_j$ represents a mean of a jth output; $\sigma_i$ represents a standard deviation of the ith input; $\sigma_j$ represents a standard deviation of the jth output; and $|S_{ij}|$ represents sensitivity of the jth output to the ith input of the medical risk process model.

* * * * *